US006748687B2

(12) United States Patent
Riley

(10) Patent No.: US 6,748,687 B2
(45) Date of Patent: Jun. 15, 2004

(54) MULTI-WEB BUSINESS FORM HAVING MOISTURE PROOF WRISTBAND, IDENTIFICATION LABELS AND WEB JOINT

(75) Inventor: James M. Riley, St. Louis, MO (US)

(73) Assignee: Laser Band, LLC, St. Louis, MO (US)

( * ) Notice: Subject to any disclaimer, the term of this patent is extended or adjusted under 35 U.S.C. 154(b) by 0 days.

(21) Appl. No.: 10/352,012

(22) Filed: Jan. 27, 2003

(65) Prior Publication Data

US 2003/0177681 A1 Sep. 25, 2003

Related U.S. Application Data

(63) Continuation of application No. 09/710,229, filed on Nov. 10, 2000, now Pat. No. 6,510,634, which is a continuation-in-part of application No. 09/489,647, filed on Jan. 24, 2000, now Pat. No. 6,438,881, which is a continuation of application No. 09/340,273, filed on Jun. 25, 1999, now Pat. No. 6,067,739, which is a continuation of application No. 09/104,292, filed on Jun. 24, 1998, now Pat. No. 5,933,993, which is a continuation-in-part of application No. 08/949,578, filed on Oct. 14, 1997, now Pat. No. 6,000,160.

(51) Int. Cl.[7] ................................................ A61B 5/117
(52) U.S. Cl. .......................... 40/633; 283/109; 283/900
(58) Field of Search ............................. 40/633; 283/74, 283/75, 80, 109, 900

(56) References Cited

U.S. PATENT DOCUMENTS

| | | | | |
|---|---|---|---|---|
| 3,197,899 A | 8/1965 | Twentier | ...................... | 40/633 |
| 4,627,994 A | 12/1986 | Welsch | ........................ | 428/41 |
| 4,682,431 A | 7/1987 | Kowalchuk | | |
| 4,696,843 A | 9/1987 | Schmidt | ................... | 428/57 X |

(List continued on next page.)

FOREIGN PATENT DOCUMENTS

GB 2045718 A 11/1980

OTHER PUBLICATIONS

Standard Register, *P.S. Magazine*, Fall 1998, Dayton, Ohio.
Gretchen Berry, "Wrist Watch", *Advance for Healthcare Information Professionals*, Feb. 15, 1999.
Sample of Standard Register Label.
"Yes, Sir, That's My Baby!", *Material Management in Health Care*, Feb. 1999, vol. 8., No. 2, Health Forum, Inc.
Brochure entitled: "Color–Bar®—Click Strip™ Labeling System"; Smead Manufacturing Company; Date Unknown; Form No. SSS–CS–00.
Brochure entitled: "Color–Bar® Folders"; Smead Manufacturing Company; Date Unknown.
Brochure entitled: "Integrated Document Management Software"; Smead Manufacturing Company; Date Unknown; Form No. SLI–95.
Catalog entitled: "Reseller Catalog Number One"; Smead Software Solutions™; Date Unknown; Form No. SSS–RC1–00.
Sample of Avery Dennison DuraCard TM.
Avery Laminated Identification Card #5361.
Sample of Standard Register Labels.

*Primary Examiner*—Joanne Silbermann
(74) *Attorney, Agent, or Firm*—Thompson Coburn LLP

(57) ABSTRACT

A multi-layer, multi-web, laser printable, form with an identification band blank comprises a multi-layered web die cut with a first paper label portion for receiving a printed image and an adhesive backed transparent film layer approximately twice the width of the paper layer so that upon separation from a carrier, the transparent film may be folded over and completely encapsulate the paper layer to moisture proof it and protect it. The transparent film layer includes a pair of adhesive backed tabs at the ends to facilitate its attachment about a patient's wrist or ankle. Multiple wristbands, or identification band blanks, are included on the same sheet to provide a form that is particularly suited for a pediatric admission. In an alternate embodiment, a panel is die cut into the transparent film layer so that upon separation of the wristband from the form, the panel remains adhered and it pulls away to form a window. As the wristband is assembled, the window overlies a portion of the printed surface so that it remains exposed.

17 Claims, 9 Drawing Sheets

U.S. PATENT DOCUMENTS

| | | | | |
|---|---|---|---|---|
| 4,854,610 | A | 8/1989 | Kwiatek | 283/81 X |
| 4,956,931 | A | 9/1990 | Selke | 40/633 |
| RE33,616 | E | 6/1991 | Welsch | 428/57 X |
| 5,026,084 | A | 6/1991 | Pasfield | 283/75 |
| 5,045,426 | A | 9/1991 | Maierson et al. | |
| 5,135,789 | A | 8/1992 | Schmidt | 428/61 X |
| 5,227,004 | A | 7/1993 | Belger | |
| 5,318,326 | A | 6/1994 | Garrison | 283/101 |
| 5,370,420 | A | 12/1994 | Khatib et al. | 283/81 |
| 5,383,686 | A | 1/1995 | Laurash | 283/81 |
| 5,418,026 | A | 5/1995 | Dronzek, Jr. et al. | |
| 5,427,416 | A | 6/1995 | Birch | 283/75 X |
| 5,486,021 | A | 1/1996 | Laurash | 283/81 |
| 5,486,436 | A | 1/1996 | Lakes | |
| 5,509,693 | A | 4/1996 | Kohls | 283/75 |
| 5,509,694 | A | 4/1996 | Laurash et al. | 283/81 |
| 5,518,787 | A | 5/1996 | Konkol | |
| 5,524,934 | A | 6/1996 | Schwan et al. | 283/95 |
| 5,547,227 | A | 8/1996 | Laurash et al. | 283/81 |
| 5,586,788 | A | 12/1996 | Laurash | 283/81 |
| 5,595,404 | A | 1/1997 | Skees | 283/116 |
| 5,598,970 | A | 2/1997 | Mudry et al. | 229/305 |
| 5,601,313 | A | 2/1997 | Konkol et al. | 283/81 |
| 5,630,627 | A | 5/1997 | Stewart | 283/81 |
| 5,637,369 | A | 6/1997 | Stewart | 283/81 X |
| 5,648,143 | A | 7/1997 | Mehta et al. | |
| 5,653,472 | A | 8/1997 | Huddleston et al. | 283/75 |
| 5,662,976 | A | 9/1997 | Popat et al. | |
| 5,687,903 | A | 11/1997 | Akridge et al. | 229/75 |
| 5,933,993 | A | 8/1999 | Riley | 40/633 |
| 6,000,160 | A | 12/1999 | Riley | 40/633 |
| 6,016,618 | A | 1/2000 | Attia et al. | 40/633 |
| 6,053,535 | A | 4/2000 | Washburn et al. | 283/81 |
| 6,067,739 | A | 5/2000 | Riley | 40/633 |
| 6,071,585 | A | 6/2000 | Roth | |
| 6,159,570 | A | 12/2000 | Ulrich et al. | |
| 6,303,539 | B1 | 10/2001 | Kosarew | |
| 6,331,018 | B1 | 12/2001 | Roth et al. | 283/81 |
| 6,361,078 | B1 | 3/2002 | Chess | 283/81 |
| 6,409,871 | B1 | 6/2002 | Washburn et al. | 40/630 X |
| 6,438,881 | B1 | 8/2002 | Riley | 40/633 |
| 6,510,634 | B1 | 1/2003 | Riley | 40/633 |
| 6,517,921 | B2 | 2/2003 | Ulrich et al. | |

MULTI-WEB BUSINESS FORM HAVING MOISTURE PROOF WRISTBAND, IDENTIFICATION LABELS AND WEB JOINT

CROSS REFERENCE TO RELATED APPLICATION

This application is a continuation of application Ser. No. 09/710,229, filed on Nov. 10, 2000, now U.S. Pat. No. 6,510,634, issued on Jan. 28, 2003; which is a continuation-in-part of application Ser. No. 09/489,647, filed on Jan. 24, 2000, now U.S. Pat. No. 6,438,881, issued Aug. 27, 2002; which is a continuation application Ser. No. 09/340,273, filed on Jun. 25, 1999, now U.S. Pat. No. 6,067,739, issued on May 30, 2000; which is a continuation of application Ser. No. 09/104,292, filed on Jun. 24, 1998, now U.S. Pat. No. 5,933,993, issued on Aug. 10, 1999; which is a continuation-in-part of Ser. No. 08/949,578, filed on Oct. 14, 1997, now U.S. Pat. No. 6,000,160, issued on Dec. 14, 1999.

BACKGROUND AND SUMMARY OF THE INVENTION

Identification bands are used in many applications, including particularly in hospitals or the like for patients upon admission. In such instances, when a patient is admitted, information is taken from the patient with respect to his medical history, and, during the course of the patient's stay, it's not unlikely that various kinds of medications and treatments are given to the patient. For these reasons, and others, it is important to keep track of the patients in a reliable manner with an identification bracelet which will withstand the vagaries of a hospital environment.

As the admission and processing of patients in hospitals becomes more automated with computers, there has developed a need in the art for an identification band which may be secured about a patient's wrist or ankle, for example, and which is readily generated through the same computer system as is used to in-process the patient himself. Commonly, and at the present time, these computer systems routinely print admission forms on laser printers.

In the prior art, identification bands have tended to be ruggedized and moisture proofed in order to insure that they are not easily removed by either the staff or the patient, inadvertently or on purpose. Additionally, various arrangements have been provided in the prior art for moisture proofing these identification bands by overlying the band with a plastic film or surrounding it in a plastic sleeve or the like. Of course, this complex structure and arrangement requires time for a medical professional not only to assemble the patient identification band but also to mark the patient identifying information to the band and apply it to the patient in a secure manner. As hospitals process patients in significant numbers, the time required to prepare including marking the band with patient information and applying patient identification bands can be significant and requires more than a minor intrusion into a medical professional's daily task. Furthermore, requiring the medical professional to apply the information manually, or in a process separate from the actual registration task increases the chance for error.

Still another problem with prior art identification bands is their relatively narrow width. This narrow width limits the font size of printing and thereby renders the band difficult to read. In many instances, the bands were hand lettered or manually typed or imprinted which created additional problems relating to the physical handling of the bands and the resulting "readability" problems caused by illegible or misaligned printing or typing.

With the advent of computer systems, including laser printers, there have been attempts in the prior art to solve these needs, with varying degrees of success. For example, U.S. Pat. No. 4,682,431 discloses a continuous form admission record with an adhesive backed patient identification band which may be removed from the continuous form after the patient's name and any identifying data is printed thereon, the band folded over on itself for adhering adhesive backed portions of the band together, and then securing the band to a patient's wrist by folding it into a loop and joining its ends by use of an adhesive tab. However, the construction of the '431 patented band has several drawbacks. One such drawback is that the data printed on the identification band remains exposed after the band is applied to a patient's wrist. While special, more expensive, types of paper or plastic stock may be used, which will help to minimize any obliteration or alteration of the data, this increases the cost of the band and does not provide a full solution. As shown in the patent, this form is made as a continuous form that is generated on a printer having minimum sizes and clarity of type font and bar code which reduce their legibility and image quality. Furthermore, as the disclosure is best understood, the adhesive tab, which secures the opposite end of the band to hold it in a loop appears to be non-overlapping such that its integrity may be readily breached.

The inventor herein is also aware of prior art identification badges or cards formed in a multi-part form wherein a paper layer provides a surface for the printing of identification information including a person's name, and a second layer of adhesive backed film is oversized so that upon separation of the badge from a carrier, the transparent film may be folded over to overlie the card. As best known to the inventor, these name badges have been used and recommended in the prior art for convention name tags, membership cards and the like which may be directly pinned onto a wearer's clothing, slipped into a plastic carrier for pinning onto a wearer's person, or carried in a wallet, or otherwise affixed with separate supporting structure. This product is available commercially under the trademark DURACARD from Avery Dennison and is apparently disclosed in U.S. Pat. No. 5,662,976.

In order to solve these and other problems in the prior art, the inventor has previously succeeded in designing and developing an identification band blank formed as part of a multi-part, standard page-sized, form which is readily adaptable for use in recording a patient's admission to a hospital or other health care facility, for example. This invention is a good and valuable invention and is the subject of the several patents noted above. With this invention, an upper portion of the page-sized form may be comprised simply of a matrix of adhesive backed identification labels which may be removed conveniently to adhere to the patient's utensils, hospital chart, room sign, etc. At the same time, another portion of this page-sized form includes multi-layered identification band blanks.

In a preferred embodiment of the prior patented invention, the page-sized form is comprised of two layers; a paper stock layer and an adhesive backed transparent film layer. The paper stock is suitable for accepting an image printed thereon by a laser printer or the like and can be relatively inexpensive paper stock as will be seen momentarily. With this construction, the band blank can be thought of as an "open system" form. By that is meant the band blank can be any standard, or special, paper or paper size for printing in any printer with any suitable ink. Preferably, a laser printer may be used.

In another preferred embodiment of the prior invention, the page-sized form is comprised from two webs, with a first web forming the upper portion and a second web forming the lower portion, the lower portion containing the multi-layered identification band blanks. These two webs may themselves be formed from different materials, as desired, to accommodate different printers, applications for users, ink requirements, strength or flexibility needs, or any other processing or use environment or need. For example, the upper portion or first web may be formed with a top layer of adhesive backed paper stock with a bottom layer of a coated liner. The lower portion or second web may be formed with a top layer of paper and a bottom layer of an adhesive backed transparent film. After the two webs are individually formed, the webs are joined such as by being overlapped and glued together along their length, and then cut to form the desired page-sized form. In either embodiment a line of perforation may be added to separate the two portions from each other so that a user may conveniently separate the portions to separate the bracelet from the labels.

In either embodiment, the outline of the paper may be kiss-cut into the paper stock such that only the paper stock portion of the multi-layer form is cut for separation from its surrounding paper layer. The transparent adhesive backed film which comprises the other half of the identification band blank is also kiss-cut but has a size more than twice the width of the paper label portion so that upon separation from the carrier, the transparent film may be folded along a fold line to completely overlay, surround, and encapsulate the paper label portion. An edge of adhesive backed film surrounds the entire circumference of the paper label so that a completely moisture-proof seal is formed. Also, each "half" of the transparent film includes an adhesive backed tab extending from its edge so that as the transparent film is folded over, the identification band blank has an adhesive backed tab at either end and aligned for securing the band blank about a patient's wrist or ankle. As each of the tabs is adhesive backed, and they are arranged to join with each other on their adhesive surfaces, a rather secure attachment is provided when the patient's wrist is appropriately sized. However, in most instances this is not the case. As each tab has its own adhesive layer, the tabs need not overlie one another and instead will attach to other parts of the band blank such that the identification band blank may also be attached conveniently to a typically sized wrist.

In an alternative construction of the prior invention, a second set of kiss-cuts, of greater strength such that they are not as readily separated, may be formed in the identification band blank and used to provide a reduced length identification band blank for children or infants, as required. With this alternative construction, reduced inventory of the page-sized forms is permitted as the form may be used for virtually any patient being admitted to the hospital or other institution.

While the prior invention has been a good and valuable invention, and an invention that has met with great commercial success and acceptance, the inventor has continued further development based on his experience and as he has applied his invention to various situations. In that regard, the inventor has identified several issues for which his prior invention has represented only a partial solution. One such issue relates to the very common situation when a pregnant mother is admitted to a medical facility or otherwise processed in connection with the birth of her baby. With the prior invention, wristbands and labels could be readily created to suit the situation, but multiple forms would be needed to be used and there would be the distinct possibility that there would be wastage and in any event there would be extra cost involved. Furthermore, the typical printer would not have sufficient tray capacity to hold and make available for automatic processing the differently sized wristbands that would be useful. For example, the baby would need one or maybe even two wristbands to fit around his/her arm and leg, a standard adult sized wristband would be useful for the father, and a standard adult sized or maybe even a somewhat smaller adult wristband would be appropriate. While these separate wristbands could be readily made available, they would each require a separate tray, along with a tray for the "regular" wristband label combination form. Alternately, the admittance clerk could re-load wristbands into the same tray as they were printed or an additional printer could be purchased and set up, but each of these alternatives represent extra expense for equipment or labor.

To solve this problem, the inventor has succeeded in designing a form that incorporates on a single sheet the necessary wristbands to satisfy the needs for admitting a pregnant mother. That includes two smaller wristbands for the baby, and two larger wristbands for the mother and father, along with a self laminating identification card which could be used as a visitors card, ID card to verify that some other family member or friend should be permitted access to the baby, or for any other suitable use recognizing that it would be printed with the authentic data generated by the admittance clerk upon patient admittance. Thus, these various wristbands are for the first time combined on a single form so that software may be conveniently written to allow its automatic processing by the admitting clerk all at the same time without re-loading paper trays on printers or requiring additional printers. This ensures that the same, and correct, identifying information is printed on the bands. This also provides additional security for the baby and family as an aid in preventing unauthorized people from gaining access to the baby and possibly kidnapping the baby. This also helps prevent any mistaken identity by the medical personnel in relating the baby to his/her correct parents and also in administering the proper medication or other treatment to the correct baby. The press has previously reported cases where two babies were switched at birth and raised by each other's families. This happenstance when later discovered has resulted in anguish for all involved and as a result has come to be a point of genuine concern for families. The present invention virtually eliminates the possibility for any inadvertent switching of babies as they will each have not one but two separate identifying bands at opposite ends of their precious bodies. Furthermore, the parents have the added confidence of seeing the same printed information on their own wristbands as is on their baby's thereby conveying a feeling of comfort and reassurance. All of these advantages are provided with the present invention.

Still another issue that has been experienced by the inventor is that bar codes are gaining more acceptance for identifying patients thus creating a need for a bar code to be printed on each wristband. While the prior invention is fully capable of receiving a printed bar code, and in most instances the printed bar code is capable of being successfully read through the protective laminate covering, it has been found that more than a few medical facilities have older bar code reading equipment which make reading the bar code problematic. Or, the bar code reading equipment may not be adequately adjusted or maintained, or for other equipment reasons there is some difficulty in reading the bar code. In some of the prior art wristbands, a single ply of material is presented without a protective covering so that the surface having the printed bar code is immediately exposed for reading. Unfortunately, these single ply wristbands are generally considered as less desirable in that only a single ply must be made of a stronger material that is capable of accepting a printed bar code, and that generally means a more expensive material than the inventors prior two ply construction. In large quantities, even a small difference in material cost can result in significant savings so there is advantage in utilizing the inventor's two ply construction. Furthermore, even with a stronger material used as the single ply, it is not nearly as strong as with the two ply (actually three ply when the clear laminate ply is doubled over the paper ply) construction found in the inventors prior wristband design. For these reasons, the inventor has sensed a need for a modification to his prior inventive design that maintains the many advantages and features that it provided but yet eliminated any actual or even perceived difficulty encountered in reading the printed bar code. To satisfy that need, the inventor has succeeded in designing and developing a different version of his wristband invention that has a die cut window in the fold over laminate portion, with a layer of adhesive being supplied under it in place of the ordinarily supplied release layer so that as the fold over laminate portion is separated from the web the die cut window remains in place and the laminate being folded over positions the window over a portion of the label ply to thereby leave exposed a printed bar code on the paper ply. With this construction, the paper label and clear laminate plies may still be used as an opening or window on only one side of the laminate does not significantly detract from the strength of the assembled wristband. Furthermore, the paper ply is preferably still adhered to the full underlying ply of laminate so that its strength is added to that of the paper. Depending on the size and shape of the window, an edge of laminate may preferably be formed at either or both of the top and bottom and allowed to overlap onto the top of the face ply to add even more strength. The paper ply itself is preferably adhered to the underlying laminate ply and this helps to keep the paper ply aligned with the window and also prevent the paper ply from moving away from the laminate as the wristband is worn. With this construction, the advantages of strength and durability of the prior invention may be maintained while the bar code may be fully exposed and thereby assured of being correctly read.

While many of the principal advantages and features have been briefly explained, a more thorough understanding of the invention may be obtained by referring to the drawings and description of the preferred embodiment which follows.

DETAILED DESCRIPTION OF THE PREFERRED EMBODIMENTS

Figure 1:
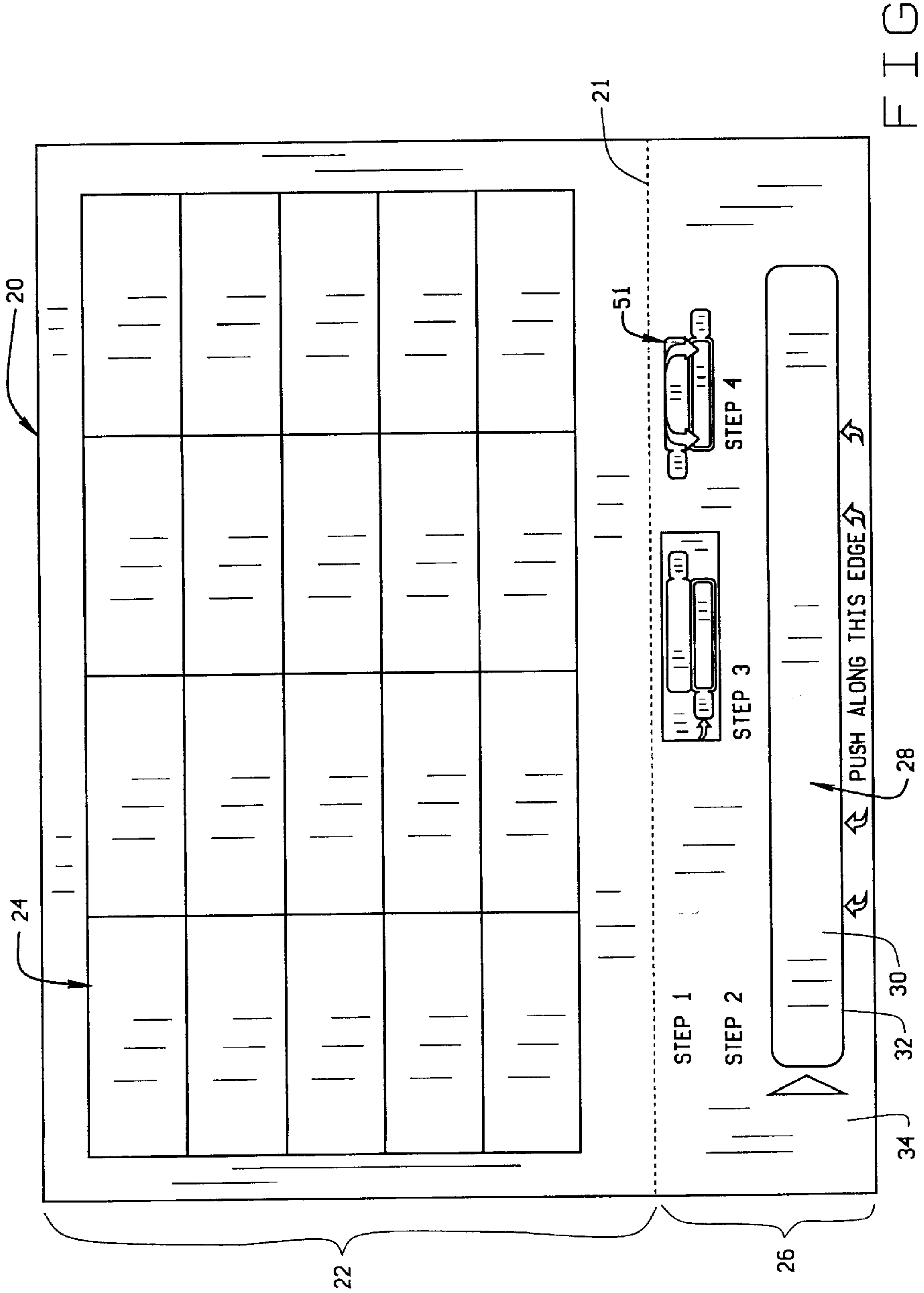
FIG. 1 is a top view of a page-sized form of the prior invention illustrating the paper, image receivable, side of the form with instructions provided for separating the identification band blank and assembling it.

As shown in FIG. 1, a page-sized, multi-layered form 20 may be suitably sized for automatic feeding in a common laser printer, as known in the art. The page-sized form 20 is divided into a first portion 22 which may be practically anything as suited to the particular application. For example, as illustrated in FIG. 1, a 4×5 matrix of individually die cut labels 24 may each be pre-printed with the patient's name, social security number, address, attending physician, date of admission, and even a bar code or other identifying indicia. These labels 24 may then be used as desired by the staff to identify the patient's articles, room, medicine containers, and other things for proper medical attention and for billing and administrative purposes as well. A second portion 26 of the form 20 includes the identification band blank 28. As viewed in FIG. 1, the paper stock element 30 is shown upon which an image may be printed by the laser printer, as mentioned above. The outline of the label 30 is defined by a dye cut 32 which may be a kiss-cut through the paper stock layer of multi-layer form 20, as known in the art. With a kiss-cut, the label portion 30 may be readily separated from the carrier 34 surrounding it and separated from it by kiss-cut 32.

Figure 3:
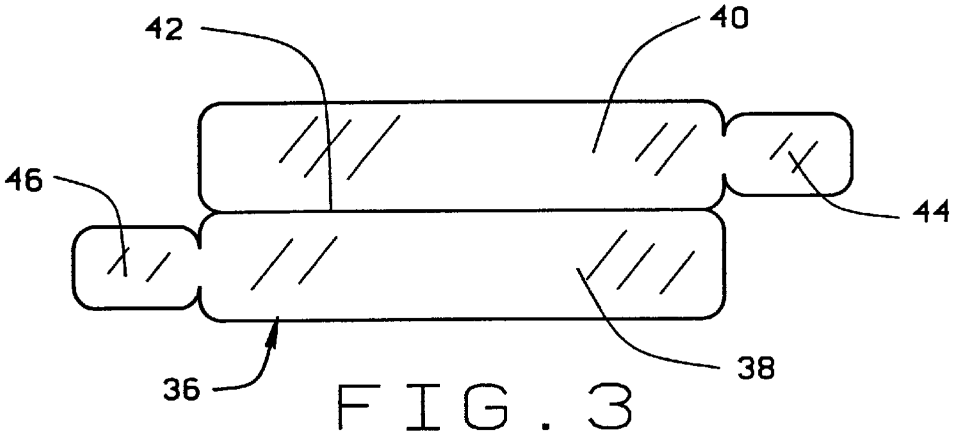
FIG. 3 is a plan view solely of the adhesive backed transparent film portion of the identification band blank.
Figure 4:
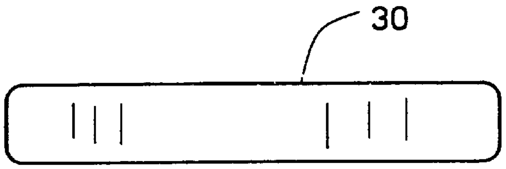
FIG. 4 is a plan view solely of the paper stock portion of the identification band blank.

As illustrated in the instructions portion shown in FIG. 1, and FIG. 3, the identification band blank 28 includes an adhesive backed, transparent film portion 36 having a lower half 38 separated from an upper half 40 by a fold line 42. Adhesive backed tabs 44, 46 are formed at one end of each of tabs 38, 40. Although not shown in FIG. 1, but similarly to the kiss-cut 32 provided to separate label portion 30 from carrier 34, another kiss-cut is made in the transparent film layer to allow for the ready separation of transparent film portion 36 from its surrounding carrier in the transparent film layer. A pair of notches 47, 49 are provided in the film portion 36 which are aligned with the fold line 42 which help to separate the film from the surrounding carrier and which also form a contour which follows the rounded edges of the paper label portion 30.

Figure 2:
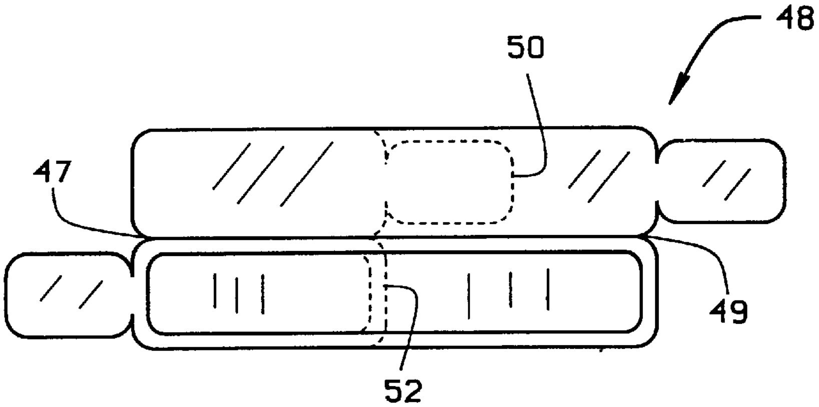
FIG. 2 is a plan view solely of the identification band blank with the additional midstrength perforations of the alternative embodiment.

An alternative embodiment 48 is shown in FIG. 2. It includes, in addition to the kiss-cuts of the preferred embodiment, a second set of mid-strength perforations 50 and 52 which allow, with somewhat greater effort, a clean tearing away of a portion of the identification band blank in order to provide a smaller length version thereof. This is particularly helpful to accommodate smaller wrists such as those of infants and children. Also, this feature permits a single page-sized form 20 to be utilized as inventory and yet provide convenient and comfortable fit of the identification band bracelet 28 about infant's wrists as well. However, it should be noted that adhesive backed tabs 44, 46 need not be affixed to each other and instead the identification band blank may overlap itself and be secured with a single tab 44 or 46.

Figure 5:
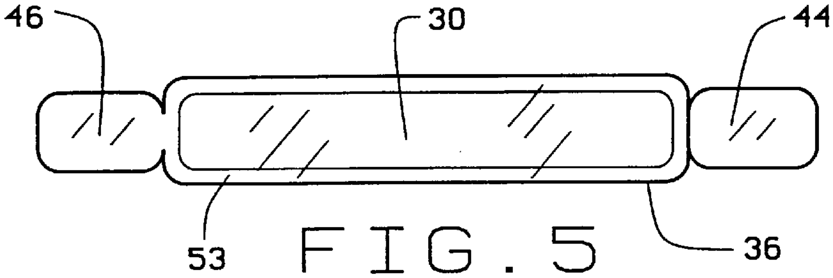
FIG. 5 is a plan view of an assembled identification band blank of the prior invention.

In operation, for example, as the form is adapted to a hospital admission of a patient, the appropriate information is taken from the patient and the computer causes the laser printer to preprint the label portion of the identification band blank. Then, following the easy instructions as shown in FIG. 1, the identification bank blank is separated both from the paper side as well as the transparent film side of the multi-layered form to arrive at a separated, but unassembled identification band blank as shown at 50. To complete the preassembly of the identification band blank, the upper half 40 of the transparent film layer is folded about fold line 42 to overlie the paper label 30 and adhere to the adhesive side of the lower half 38. This completed construction is shown in FIG. 5. As shown therein, the paper label portion 30 has a silhouette which is narrower than the width of the folded over transparent film layer such that an adhesive-to-adhesive seal completely surrounds and encapsulates the paper label portion 30. In other words, a picture frame 52 of sealed halves of the transparent film surround the paper label portion 30. This provides optimum moisture proofing and a protective layer of transparent film overlying the laser printed information contained in the identification band blank.

The identification band blank may then be applied to a patient's wrist by looping it therearound, overlapping tabs 44, 46, such that their adhesive surfaces align with each other and are secured to each other. This provides maximum sealing and fastening strength, which, although not completely tamperproof, requires a concerted effort in order to separate and remove the identification band blank. For patients with smaller wrists, the band blank may be overlapped as it encircles the wrist and the tabs adhered to the body of the band blank.

Figure 6:
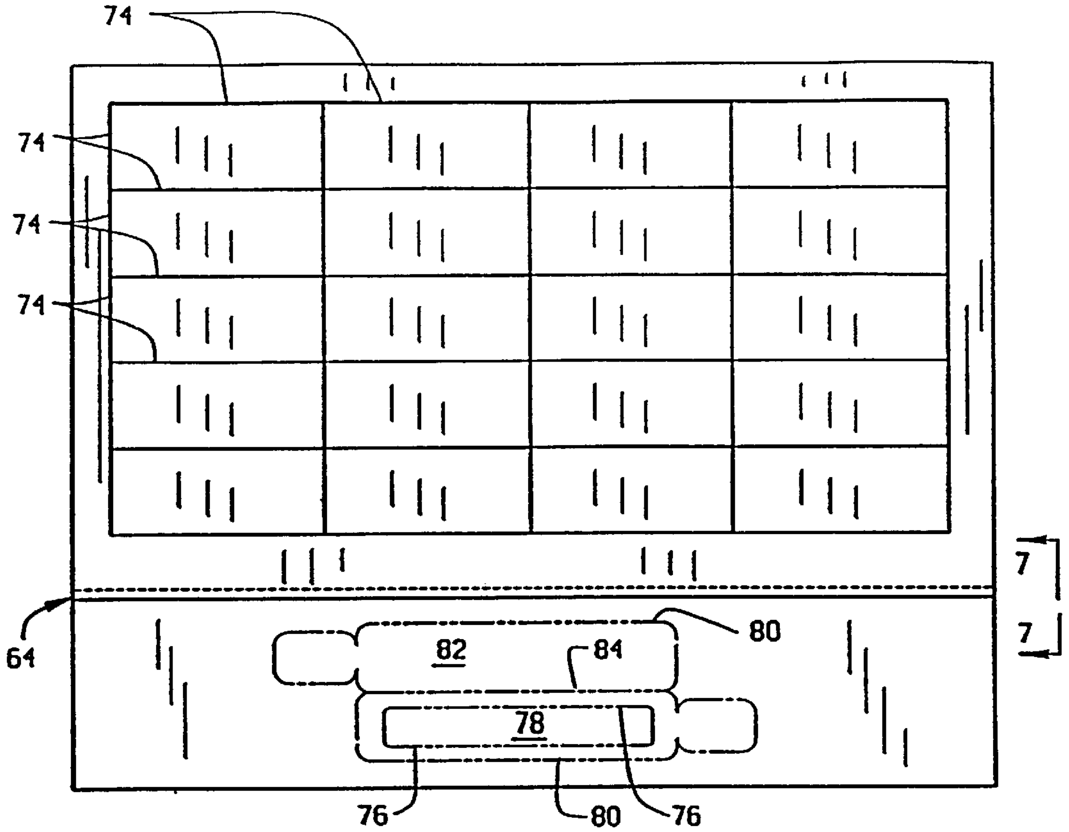
FIG. 6 is a plan view of another embodiment of the prior invention utilizing two webs glued together to construct the page-sized form.
Figure 7:
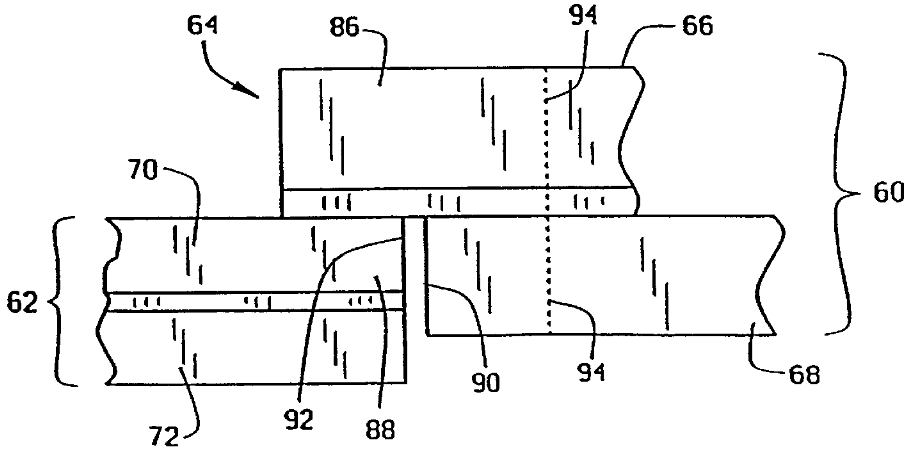
FIG. 7 is a partial cross-sectional view taken along the plane of lines 7—7 in FIG. 6 and further detailing the glued joint between the two webs of the embodiment of FIG. 6.

Still another embodiment of the form is shown in FIGS. 6 and 7. In this embodiment, two separate webs 60, 62 are preferably separately formed and joined together at a joint 64, which preferably is a lapped and glued joint, with each web 60, 62 being preferably comprised of two layers of material chosen from a number of materials as desired by a user and to suit any particular application as would be known to those of skill in the art. By way of example only, and not to be limiting in any sense, the first web 60 may preferably be formed by a top layer 66 of an adhesive backed paper stock and a bottom layer of a liner 68. The second web 62 may preferably be formed by a top layer 70 of a somewhat thinner liner paper suitable for accepting laser printing and a bottom layer 72 of an adhesive backed transparent film or vinyl which exhibits moisture resistance and tearing. As in the other embodiments of the present invention, the top layer 66 of the first web 60 may preferably be die cut along lines 74 into a matrix, such as a 4×5 matrix as depicted in FIG. 6, of self adhesive labels which may be printed with a patient's name, social security or other identifying number, address, medical information, or other desired information for use as a supplement to the band blank of the second web 62. More particularly, and without limiting in any sense, the second web 62 may preferably have its top layer 70 die cut along line 76 to form the paper label portion 78 of the band blank which receives the printing from the laser or other computer controlled printer (it being understood that a laser or any other presently known or later developed computer controlled printer could be used to print the band blanks of the present form as would be well known to those of ordinary skill in the art). The bottom layer 72 may preferably be die cut along line 80 which is a peripheral line surrounding the transparent layer 82 which separates from layer 72 as previously explained to encapsulate the paper label portion 78 of the band blank. A line 84 of perforation essentially dissects the transparent layer 82 and provides a guide for folding over the transparent layer 82 to encapsulate the paper label portion 78 and form the completed band blank.

As shown in greater detail in FIG. 7, the joint 64 is preferably formed as an overlapping and glued joint between the layers of the two webs. As shown therein, the top layer 66 has an overlapping flap 86 of adhesive backed paper stock which overlies corresponding shelf portion 88 of the top layer 70 of the second web 62 to which it adheres. The two webs 60, 62 may preferably be aligned to create the joint by the physical abutment of the edge 90 of the bottom layer 68 of the first web 60 with the edge 92 of the second web 62, or otherwise as would be known to those of ordinary skill in the art. A line of perforation 94 may preferably be cut into both layers 66, 68 forming first web 60 to facilitate the separation of the upper portion of the form from the bottom portion of the form, as desired. However, it may not be necessary for the perforation line 94 to be provided as the self adhered flap 86 may be lightly enough adhered to the shelf portion 88 so that it may instead be peeled off to thereby separate the two webs 60, 62. Presumably, this separation would occur after the form has been printed by the user. With this construction, the two webs 60, 62 are preferably separately formed and later assembled into a single web which may then be cut to length to form the page-sized forms. By page-sized it is meant any size as would be conveniently processed in a single pass through any printer. For example, page-sized could include standard letter size, legal size, A4 size, 11×7 size, etc., subject only to the processing capability of the particular printer chosen for use with the form. Should different materials be required for any particular application, it is then only necessary for one of the webs to be modified, and the modified form may then be conveniently assembled as before with perhaps one of the webs remaining as previously constructed. Thus, greater flexibility is provided with this embodiment.

In some applications, it may be desirable to utilize only the web which contains the band blank. In these instances, it is anticipated by the user that the associated self adhering labels which are so convenient are not needed for any number of reasons such as for outpatient processing where there will not be any utensils or other articles assigned to the patient which need to be marked with the patient's name. For these situations, the form may be sized for processing through the envelope tray of the printer, or a dummy second web joined to the band blank web to render it page sized, or the form modified as desired to be conveniently processed by any particular printer as would be readily apparent to one of ordinary skill in the art. In such instances, the band blank web would preferably comprise the only functioning portion of the form and the printer would preferably print solely onto the band blank. This embodiment of the present form provides the flexibility for the form to be used in these applications without cutting the excess portion of the form away, or without wasting the other web if left intact. Furthermore, from a production standpoint, a manufacturer need only manufacture the single band blank web of this embodiment to satisfy the need for these applications in addition to those for which the page-sized form is desired.

The joint 64 between the two webs 60, 62 is preferably a lapped, glued joint as shown and described above. However, the two webs may be joined in any alternative fashion, as would be well known to those of ordinary skill in the art. For example, the two webs may be joined without overlap, they may be joined with a binder tape overlapping both of the webs, the other web may overlap, or they may be joined in any other convenient way which would accommodate the relatively jam-free processing of the form by the printer selected for use. One of the limitations associated with present day single page, automatic feed printers is that they have a relatively complex paper path which may lead to jamming or misfeeding of a page sized form should there be a varying thickness across the sheet. As can be appreciated, with the present form this varying thickness is controlled by thoughtful selection of the materials which form the webs. The same considerations apply when selecting the joint used to join the webs.

Still another consideration in utilizing the present invention in automatic feed printers is the possibility of jamming due to adjacent sheets becoming attracted to each other through build up of static electricity, heat, or through other conditions. Again, with this embodiment of the present form these kinds of problems are readily solved by those of ordinary skill in the art and with increased flexibility through proper selection of materials for forming the webs. The inventor has found that different printers exhibit different levels of tolerance for different materials so that one grouping of materials chosen may work well for one manufacturer's printer and not so well in another manufacturer's printer. These kinds of adjustments in choosing and adapting materials for a particular printer are considered to be within the abilities of one of ordinary skill in the art.

Figure 8:
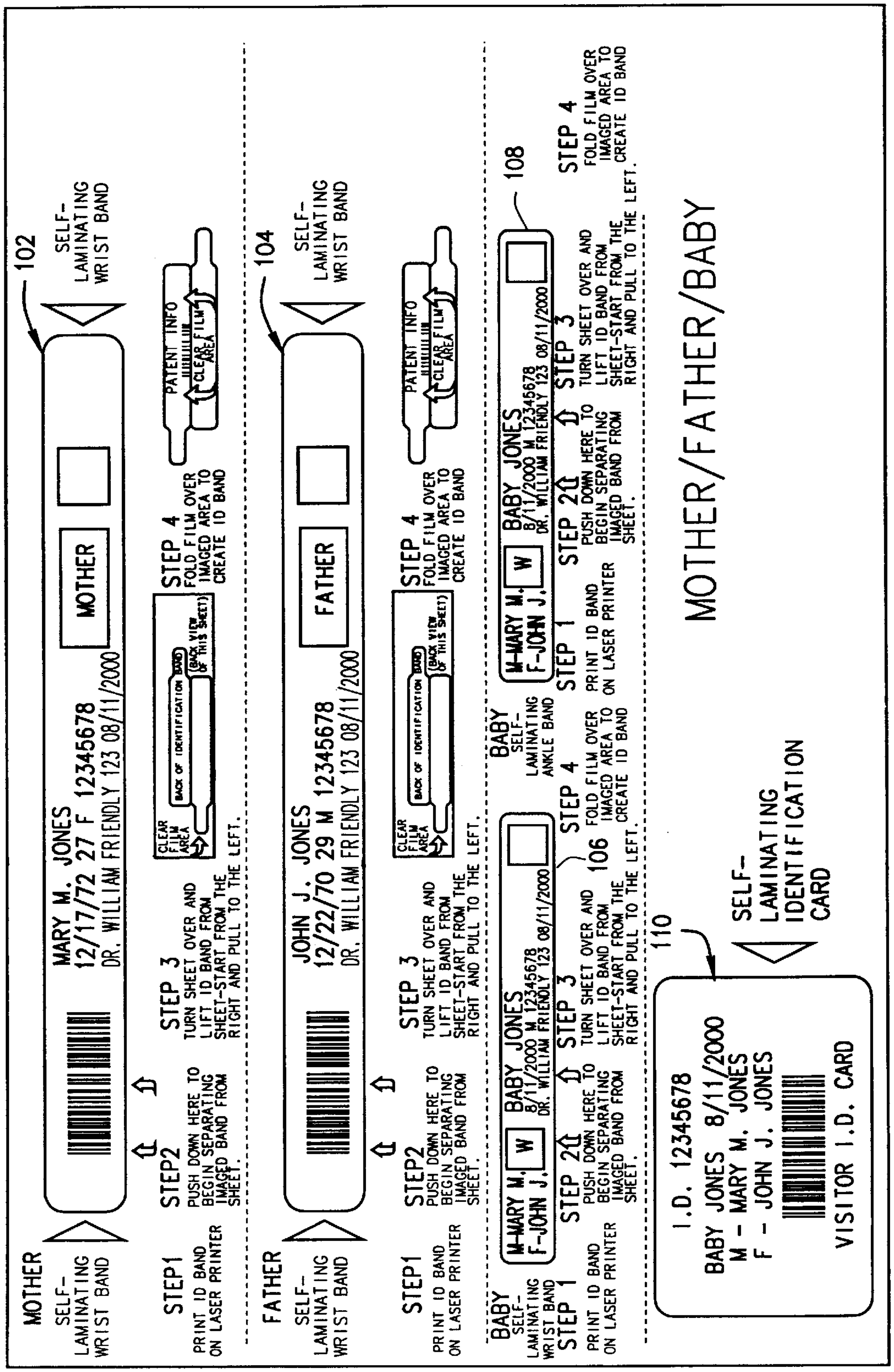
FIG. 8 is a top view of a form having a plurality of wristbands having different sizes along with an identification card.

Still another embodiment of the present invention is shown in FIG. 8 and includes a plurality of wristbands or identification band blanks 100 of different length. As shown by FIG. 8, a page-sized form may be comprised of wristbands and an identification card, with the self-adhesive labels shown in the prior embodiments being eliminated. More particularly, two wristbands 102, 104, are sized to fit a typical adult. However, a pair of smaller wristbands 106, 108 are also included. These smaller wristbands 106, 108 are suitably sized to fit around the wrist and/or ankle of a baby and especially a newborn baby. Thus, this present form, representing a single sheet which may be printed through a single pass through a printer, may be used to create wristbands to identify a father, mother, and their newborn baby with the newborn baby being double protected by having a wristband around its ankle and wrist. Alternatively, the second wristband may be saved and used to replace the first wristband as needed or desired such as for example should the first wristband become inadvertently detached. As a further feature of the present invention, a self-laminating identification card 110 having a construction similar to that of the self-laminating wristbands 102–108 may be provided and used to identify a visitor. Alternately, the identification card may merely be self-adhering much as the self-adhering labels shown in the prior embodiments hereof, or constructed of other materials such as plastic.

The single form shown in FIG. 8 thus provides a plurality of self-laminating wristbands which may be printed at the same time by a single pass through a laser printer or the like. This ensures that the correct information is printed on each of the wristbands and that they are capable of being cross-checked against each other at the time that they are created. This helps to ensure proper identification with reliably printed materials that are correctly marked so as to virtually eliminate any possibility for misidentification of a baby. This not only is helpful to the hospital or other medical facility, but also to the parents as they can be constantly reassured by glancing at the wristband around their own wrist. Furthermore, although the form of FIG. 8 shows a single self-laminating identification card which also is printed in the same single pass through the printer, an alternate construction could include multiple identification cards of different construction such as merely being self-adhering which would facilitate their being printed along the lower portion of the form as shown in FIG. 8. Still another alternative construction would delete the identification card, leaving the multiple wristbands only on the sheet sized form.

Figure 9:
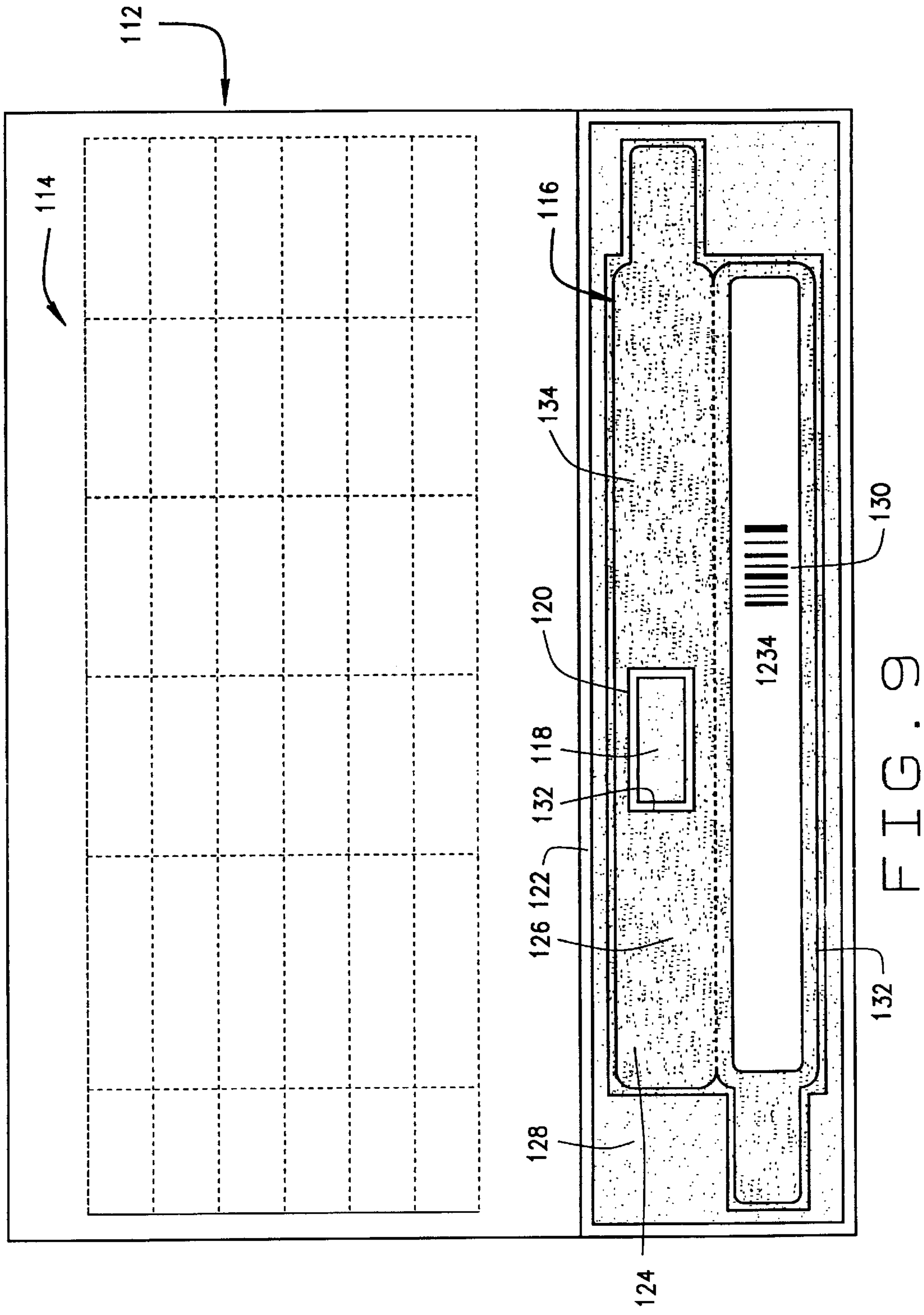
FIG. 9 is a partial back view of a wristband portion of a form with the wristband having a panel defined by a die cut and with the panel adhered to the form so that it separates upon separation to form a window in the second layer of the wristband

As shown in FIG. 9, still another embodiment of the present invention is disclosed. In that figure, a single sheet 112 may typically include a plurality of self-adhering labels 114 as well as a self-laminating wristband 116. However, in the self-laminating wristband 116 of this embodiment, a panel 118 is defined by a die cut 120 surrounding it in the transparent film layer 122. A layer 124 is applied to the form and allows that portion 126 of the transparent film layer 122 which forms the overlay for the self-laminating wristband 116 to readily separate from the form when it is desired to be assembled. However, the silicon layer 124 does not extend under the panel 118 and instead the full faced adhesive layer 128 applied to the entirety of the transparent film layer 122 adheres panel 118 to the upper layer of the form. The silicon layer 124 may extend to surround the periphery of panel 118, or alternately the full-faced adhesive layer 128 may be patterned appropriately. As shown in FIG. 9, the panel 118 is located at approximately the mid-point of the wristband 116 and is positioned to overlie a printed area 130 of the upper layer or first layer 132 formed as part of the wristband 116. This printed area 130 is thus exposed when the wristband 116 is separated from the form and assembled. While any particular printed matter may be placed in this "window" 132 formed in the transparent film layer 126 upon its separation, the inventor has found that it is convenient to place a bar code in this area so that the bar code readers may readily read the bar code without any potential interference from the transparent film overlay. Of course, other printed matter may also be printed in this same space. It is also noted that the panel 118 is sized to fit within the borders of the upper portion 134 of the transparent film overlay 126. This ensures that a portion of the overlay 134 connects both sides of the overlay portion 134, which improves the integrity of the wristband 116, as can be appreciated by those of skill in the art. Furthermore, this is seen to be an aid in assembly of the wristband form 116. Alternately, the panel 118 and corresponding window opening 132 created thereby may be adjusted in size and position to suit the form designer's needs and preferences.

Figure 10:
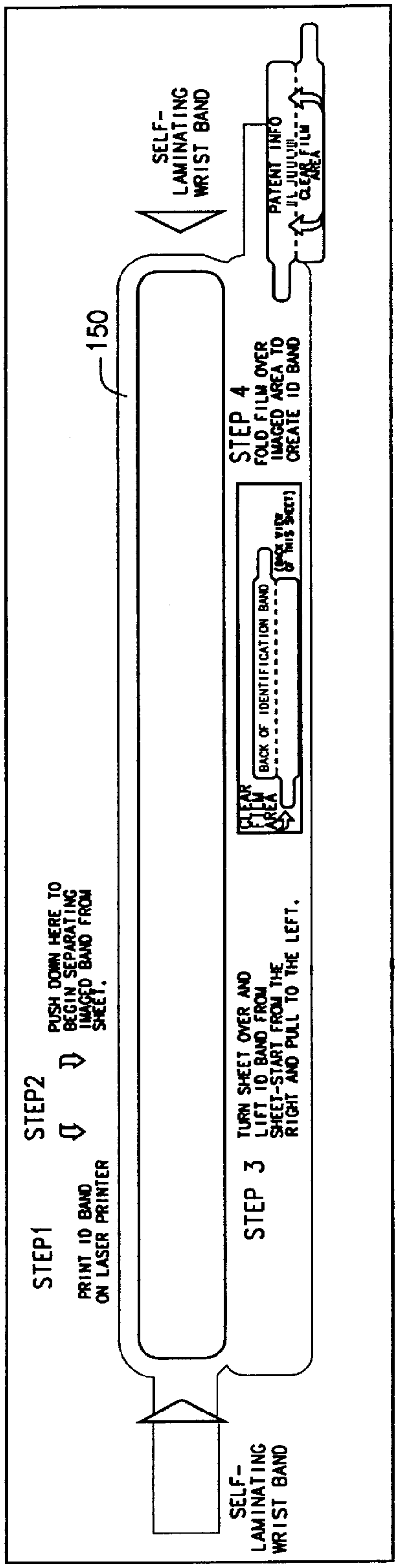
FIG. 10 is a top view of a single, full sized identification band blank only on a strip sized sheet.
Figure 11:
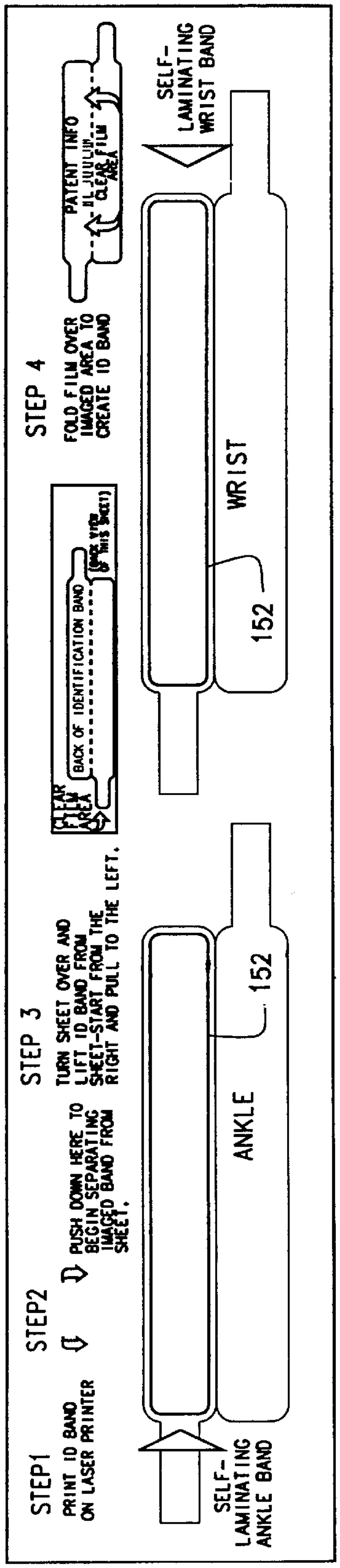
FIG. 11 is a top view of pair of smaller sized identification bank blanks on a strip sized sheet.
Figure 12:
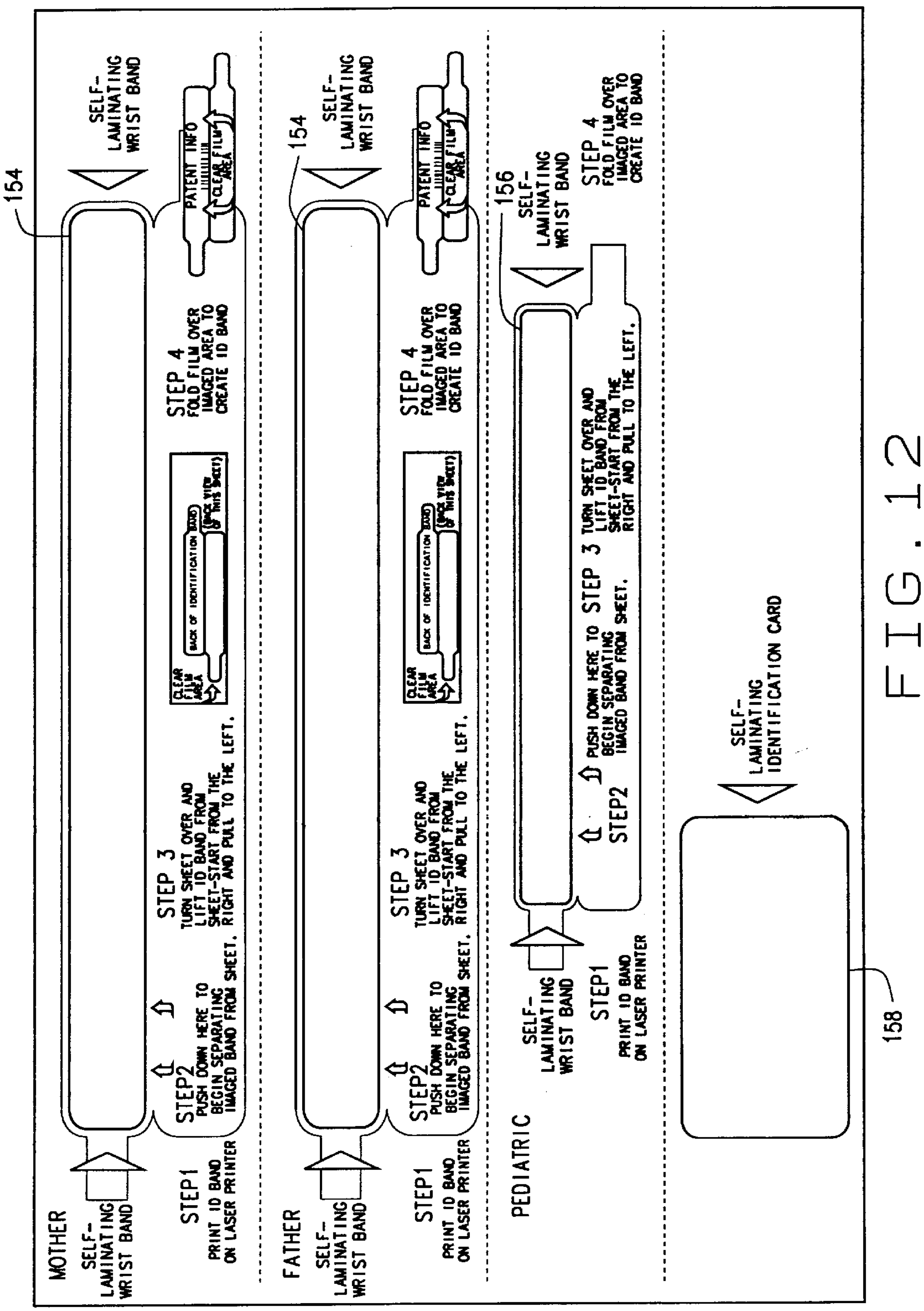
FIG. 12 is a top view of a page sized sheet with multiple sized identification band blanks including an identification card.
Figure 13:
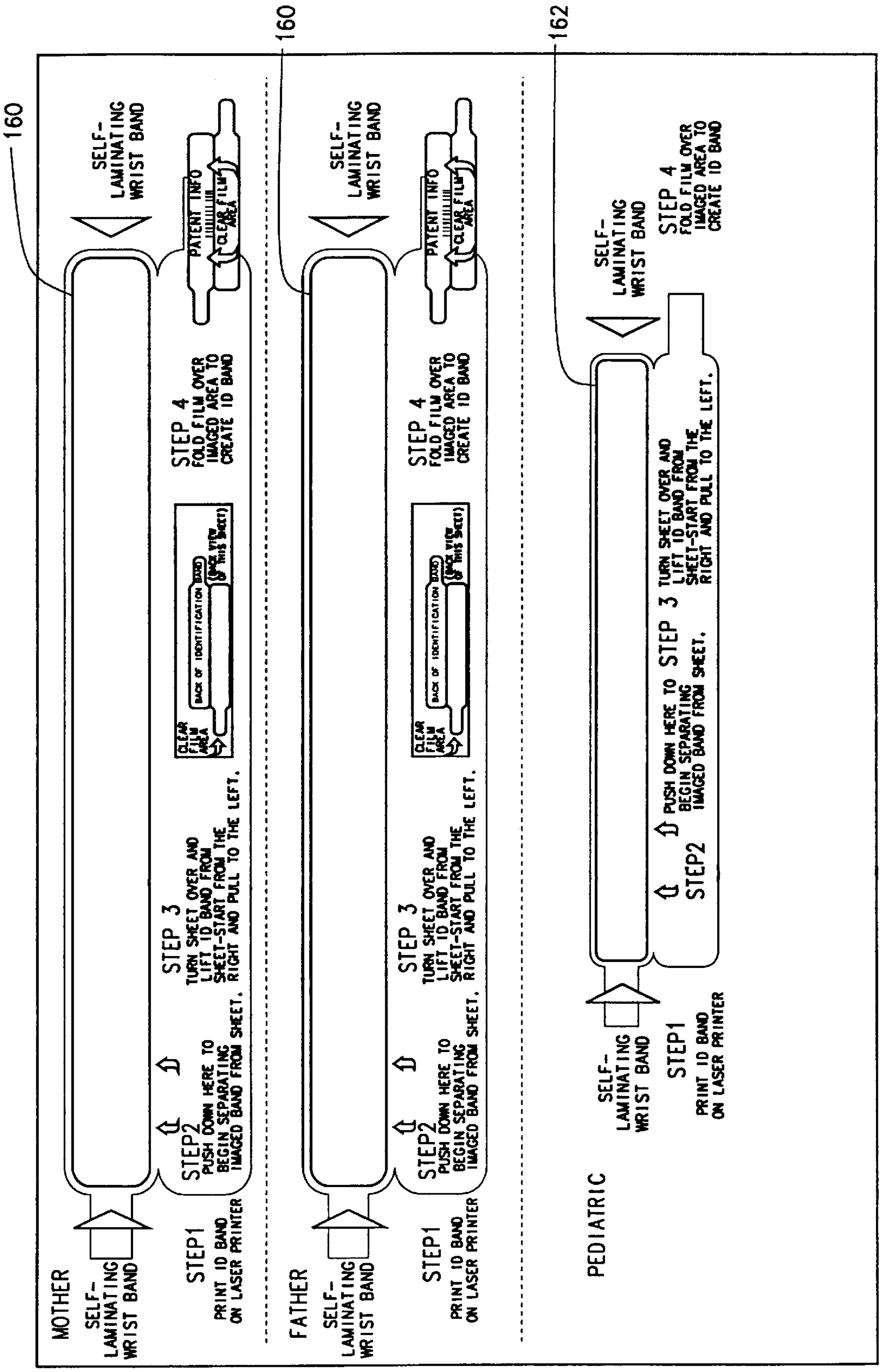
FIG. 13 is a top view of a page sized sheet with multiple sized identification band blanks without an identification card.
Figure 14:
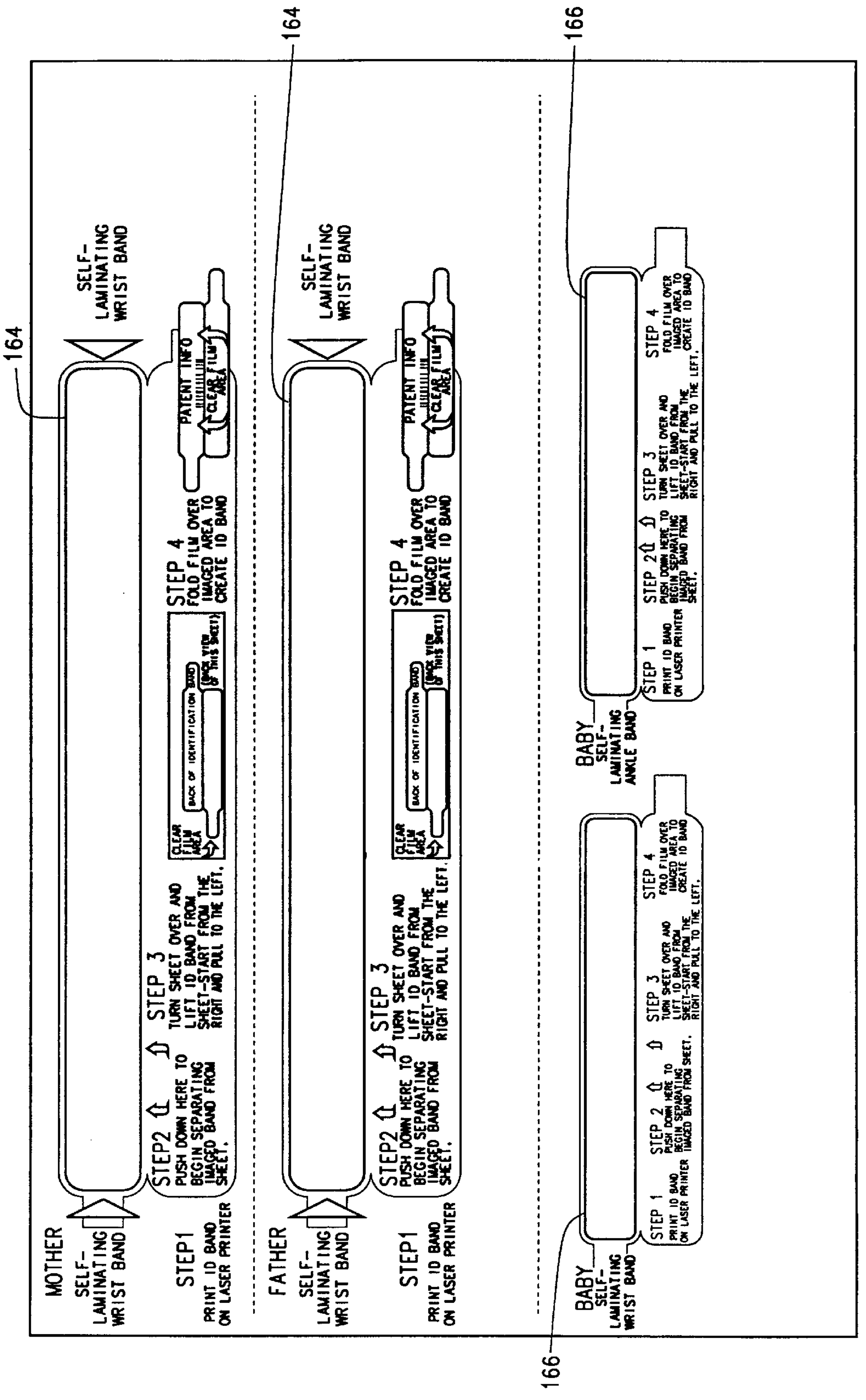
FIG. 14 is a top view of a page sized sheet with two pairs of differently sized identification band blanks with no identification card.

As shown in FIG. 10, the identification band blank 150 may be provided in a smaller sized strip or envelope sized strip form, as desired by the user and to allow for its use and feed through the envelope tray of a printer. Similarly, as shown in FIG. 11, a pair of smaller sized identification band blanks 152 may also be provided in a smaller sized strip or envelope sized strip form. These may preferably be individually marked for the ankle and wrist of an infant, if desired. Still another variation possible is shown in FIG. 12 and includes a pair 154 of adult sized and a single 156 child sized identification band blank along with a self laminating identification card 158. FIG. 13 depicts another variation which includes a pair 160 of adult sized and a single 162 child sized identification band blank with no identification card. Yet another variation is shown in FIG. 14 and it includes a pair 164 of adult sized and a pair of child sized 166 identification band blanks with no identification card. These arrangements help to show the versatility of the present invention and its adaptability to various applications to suit individual needs of the healthcare market, as well as other markets.

Various changes may be made to the invention as would be apparent to those skilled in the art. For example, the location of the differently sized wristbands as shown in FIG. 8 may be changed. Also, the wristbands may be sized in other combinations to suit other particular applications. One such example would be a form having a range of sizes including larger down to smaller. This form would be especially useful in a pediatric admission application as the child being admitted could be a small child or a large teenager. As previously mentioned, the identification card also included on the form may either be eliminated or presented in different construction such as being self-adhering instead of having a laminating overlay, made of different materials such as plastic, etc. With respect to the embodiment shown in FIG. 9, the size and location of the panel/window may be adjusted or changed to suit the designer's preferences. While the window is preferably separated from the second layer as it is separated from the form, it may instead be desirable to allow for the later separation of the panel for example after the wristband is assembled. Furthermore, the self-laminating wristband with window may be included on a form sheet having self-adhering labels as in other embodiments, separately on a form by itself, in combination with other differently sized wristbands as shown in FIG. 8, or otherwise as would be desired by the form designer to suit the particular application at hand. The preferred embodiments are shown in the context of a "page" sized form. It would be understood by those of skill in the art that the page could be A4, legal, letter size, or otherwise sized to fit and be dispensed conveniently from a printer, and preferably a laser printer.

What is claimed is:

1. An identification band blank cut into and removable from a multi-layered form suitable for processing through a printer, said multi-layered blank having a first layer suitable for receiving a print image from said printer, and a second, over-sized layer of moisture resistant material for overlying said first layer upon removal and assembly of said blank, said second layer having a panel formed and configured so that as the band blank is removed from said form said panel is separated from the second layer and a window is opened up in said second layer of said separated band blank.

2. The form of claim 1 wherein said panel is formed by a die cut into said second layer.

3. The form of claim 2 wherein said panel is positioned in said second layer to overlie at least a portion of an image printed on said first layer as the second layer is folded over said first layer.

4. The form of claim 1 further comprising a plurality of adhesive backed labels formed therein.

5. The form of claim 1 wherein said panel is generally rectangular in shape with its longer sides being parallel to the length of the band blank.

6. The form of claim 1 wherein said panel is defined by a die cut substantially surrounding it.

7. A multi-layered page-sized form suitable for processing through a printer comprising:

a first portion comprising a plurality of self adhering labels;

a second portion comprising a multi-layered identification band blank cut into and removable from the second portion, said multi-layered identification band blank having a first layer suitable for receiving a print image from said printer, a second oversized layer of moisture resistant material being approximately twice the size of said first layer, and a pair of integrally formed adhesive backed tabs are cut into and formed out of the material comprising the second layer near the ends of said band blank so that upon removal of said band blank from said second portion, the second layer may be folded over to overlie the printed image on the first layer and the tabs used to secure the band blank about a person's appendage; and a web joint connecting the first and second portions of the form together, the web joint comprising a flap extending from the form first portion to the second portion.

8. The form of claim 7 wherein the form first portion further comprises a top adhesive layer and bottom liner layer and the web joint flap comprises an extension of the top adhesive layer overlying a section of the form second portion adjacent the first portion.

9. The form of claim 8 wherein the web joint further comprises a line of perforation extending through the form first portion adjacent the flap thereby allowing the separation of the first portion from the second portion with the overlapping flap attached to the second portion.

10. The form of claim 8 wherein the web joint flap further comprises a lightly adhered layer on its underside thereby allowing the form first portion to be peeled from the form second portion.

11. The form of claim 7 wherein said web joint overlapping flap comprises a binder tape releasably attached to both the first and second portions of the form.

12. The form of claim 11 wherein the form second portion further comprises a top layer and bottom transparent layer and the web joint flap comprises an extension of the top adhesive layer overlying a section of the form first portion adjacent the second portion.

13. The form of claim 11 wherein the web joint flap further comprises a lightly adhered layer on its underside thereby allowing the form second portion to be peeled from the form first portion.

14. The form of claim 11 wherein the web joint further comprises a line of perforation extending through the form second portion adjacent the flap thereby allowing the separation of the second portion from the first portion with the overlapping flap attached to the first portion.

15. The form of claim 7 wherein the web joint is adapted to permit detachment of the first portion from the second portion at the web joint and attachment of a dummy portion to the second portion, the dummy portion being dimensioned to create a paged sized form when attached to the second portion.

16. The form of claim 7 wherein the web joint is adapted to permit detachment of the second portion from the first portion at the web joint and attachment of a dummy portion to the first portion, the dummy portion being dimensioned to create a paged sized form when attached to the first portion.

17. The form of claim 7 wherein the second portion is dimensioned to be processed through an envelope feeder of a printer when detached from the form first portion.

* * * * *